United States Patent
Garrett

(10) Patent No.: US 9,961,927 B2
(45) Date of Patent: May 8, 2018

(54) SYSTEMS AND METHODS OF MICROBIAL STERILIZATION USING POLYCHROMATIC LIGHT

(71) Applicant: Hyper Light Technologies, LLC, Nashville, NC (US)

(72) Inventor: Kurt A. Garrett, Raleigh, NC (US)

(73) Assignee: Hyper Light Technologies, LLC, Nashville, NC (US)

( * ) Notice: Subject to any disclaimer, the term of this patent is extended or adjusted under 35 U.S.C. 154(b) by 0 days. days.

(21) Appl. No.: 15/712,559

(22) Filed: Sep. 22, 2017

(65) Prior Publication Data

US 2018/0007936 A1 Jan. 11, 2018

Related U.S. Application Data

(63) Continuation-in-part of application No. 15/223,909, filed on Jul. 29, 2016, now Pat. No. 9,801,966, which is a continuation-in-part of application No. 14/815,519, filed on Jul. 31, 2015, now abandoned.

(51) Int. Cl.

| | |
|---|---|
| *A61L 2/00* | (2006.01) |
| *G01N 23/00* | (2006.01) |
| *A61N 5/00* | (2006.01) |
| *A23L 3/26* | (2006.01) |
| *B65B 55/02* | (2006.01) |
| *C02F 1/32* | (2006.01) |

(52) U.S. Cl.
CPC ............... *A23L 3/26* (2013.01); *B65B 55/02* (2013.01); *C02F 1/32* (2013.01); *C02F 2201/328* (2013.01); *C02F 2303/04* (2013.01)

(58) Field of Classification Search
CPC ..... A61L 2/00; A61L 9/00; A61L 9/18; A61L 9/20
USPC ...................... 422/22, 24; 250/455.11, 492.1
See application file for complete search history.

(56) References Cited

U.S. PATENT DOCUMENTS

| | | | |
|---|---|---|---|
| 4,871,559 A | 10/1989 | Dunn et al. | |
| 5,786,598 A | 7/1998 | Clark et al. | |
| 6,730,265 B2* | 5/2004 | Horton, III | ............. A61L 9/205 250/455.11 |
| 9,801,966 B2* | 10/2017 | Garrett | ...................... A61L 2/10 |

(Continued)

FOREIGN PATENT DOCUMENTS

| | | |
|---|---|---|
| GB | 2517022 A | 2/2015 |
| WO | 01/91810 A1 | 12/2001 |
| WO | 03/066108 A1 | 8/2003 |

*Primary Examiner* — Monzer R Chorbaji
(74) *Attorney, Agent, or Firm* — James G. Passé; Passé Intellecutal Property, LLC

(57) ABSTRACT

The present invention is a device for sterilizing microorganisms on a liquid or solid substrate. The device includes a light source for producing a light and an optical device positioned proximate the light source. The optical device is configured to focus the light generated by the light source to provide a high intensity light output. The optical device also includes a dichroic reflector. The dichroic reflector is configured to pass thermal energy generated by the light source and reflect the light produced by the light source. The device also includes a power supply, where the power supply is coupled to the light source and the optical device. The device thereby killing microbial organisms presented within the range of the high intensity light output.

14 Claims, 2 Drawing Sheets

(56) References Cited

U.S. PATENT DOCUMENTS

| | | |
|---|---|---|
| 2003/0064001 A1 | 4/2003 | Fries et al. |
| 2003/0086817 A1 | 5/2003 | Horton, III |
| 2010/0222852 A1 | 9/2010 | Vasily et al. |
| 2013/0119265 A1 | 5/2013 | Anderle et al. |

* cited by examiner

SYSTEMS AND METHODS OF MICROBIAL STERILIZATION USING POLYCHROMATIC LIGHT

This application is a continuation-in-part of U.S. Non-provisional patent application Ser. No. 15/223,909 filed on Jul. 29, 2016 which is a continuation-in-part of U.S. Non-provisional patent application Ser. No. 14/815,519 filed on Jul. 31, 2015, now abandoned, which are incorporated herein in their entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to a device for sterilizing microorganisims. In particular, it relates to a device for treatment of a patient for the purpose of killing microorganisms.

Description of Related Art

Microbiological sterilization has been pivotal in the production of biological products with extended storage times. Various technologies have been developed to achieve this sterilization, including UV-irradiation, gamma-ray irradiation (or gamma irradiation), chemical sterilization, heat sterilization, autoclaving, and ultrafiltration. Because these technologies destroy microorganisms, they are inherently damaging to other biological components that may be in the product to be sterilized. In light of this fact, a particular technology may not always be acceptable for sterilizing a given biological product. Recently, an increase in the number and variety of biotechnology products has created a need for adequate sterilization without the damaging side-effects to the desirable components of the product. These biotechnology products are often extremely labile, requiring special handling and storage conditions to retain their activity. Of the sterilizing technologies previously cited, several are not acceptable for these biotechnology applications. Chemical sterilization, heat sterilization, and autoclaving all damage or alter biological molecules, rendering them inactive. The inactivation of biological molecules effectively kills the microbe that utilized these molecules for life processes. However, this inactivation of biological molecules that occurs with prior art technologies is inherently problematic in that it may also inactivate the desired molecule or molecules contained in the biotechnology product, thus defeating the purpose of the sterilization.

Ultrafiltration, a recent technology relative to the others mentioned here, requires the use of filters with a very minute pore-size (at least <0.45 microns). These filters are an inherently slow means of sterilization, and may not be suitable for solutions of high viscosity or solutions that contain desirable particles, such as cells, that are larger than the pore diameter and, consequently, too large to pass through the filter. Gamma-irradiation is a technology not commonly used for microbial sterilization, although it can be used to ensure the sterility of the majority of, if not all, biotechnology products. One major reason for its lack of widespread use for microbial sterilization is that it utilizes a radiation source, such as radioactive cobalt, that is very radioactive, and thus, very dangerous. This technology requires extensive shielding and control systems to prevent accidental exposure to operators and others. These protective requirements are economically expensive, often prohibitively so. Therefore, gamma-irradiation is often not an economically acceptable technology or a safe technology for sterilization of biotechnology products. Additionally, gamma-irradiation sterilizes products by lysising the biological molecules contained in microorganisms. This photochemical mechanism of sterilization may also degrade the desired product, rendering it inactive, and thus defeating the purpose of the sterilization.

UV-irradiation has been used extensively for microbial sterilization. UV light breaks the hydrogen bonds between adenine-thymine moieties in the DNA polymer that comprises the genome of the cell or virus, and catalyzes the formation of a cyclobutane dimer between adjacent thymine moieties. This disruption of the genome blocks the replication cycle of the cell or virus, effectively inhibiting growth of the organism.

Generally, devices that use UV light to sterilize products are composed of a power supply (ballast), a UV light source, a light-focusing and/or light-conducting device, a light filter, and a control system to assure proper operation. The ballast is designed to supply power to the lamp in a reliable fashion in order to ensure continuous optimal function of the lamp. A variety of UV light sources exist and are known in the prior art, including pulsed, gas-filled flash lamps, spark-gap discharged apparatus, or low-pressure mercury vapor lamps. Traditionally, low-pressure mercury vapor lamps have been used for microbial sterilization devices because these lamps are relatively inexpensive to operate and emit relatively higher amounts of UV irradiation than other sources. Other types of vapor lamps are also used, including mercury-xenon (HgXe) lamps. In particular, a preferred embodiment, according to the present invention, employs a pencil type Hg(Ar) spectral calibration lamp. These lamps are compact and offer narrow, intense emissions. Their average intensity is constant and reproducible. They have a longer life relative to other high wattage lamps. Hg(Ar) lamps of this type are generally insensitive to temperature and require only a two-minute warm-up for the mercury vapor to dominate the discharge, then 30 minutes for complete stabilization.

By way of background, light is conventionally divided into infrared light (780 nm to 2600 nm), visible light (380 nm to 780 nm), near UV light (300 nm to 380 nm), and far UV light (170 nm to 300 nm). Most UV lamp sources emit light at discrete wavelengths and include filters to filter out or block wavelengths other than the specific UV wavelength, especially 254 nm. In the UV region, the most notable UV emission occurs at 254 nm. It is known that mercury vapor lamps emit radiation at 254 nm. This wavelength can damage the genome of cells and viruses, thus inhibiting their replication, thereby sterilizing the cells and viruses. Therefore, generally in the prior art, a single wavelength detector, tuned to 254 nm, has been used to determine the amount of UV radiation reaching the target. In order to optimize the UV light output efficiency of the lamp source, at least one filter was interposed in the light path in order to block non-UV light from reaching the target, allowing only UV and proximate-UV light to reach to target. Therefore, the industry has evolved over time with the solidly established paradigm that 254 nm is the sole and exclusive wavelength of importance for UV sterilization. As such, the prior art teaches away from the inclusion of non-UV wavelength light for microbial sterilization apparatus. Furthermore, this paradigm not only teaches that polychromatic or broad spectrum light as irrelevant or unimportant, but disadvantageous.

In sharp contrast to UV irradiation, which utilizes a photo thermal and/or photochemical mechanism, Dunn (U.S. Pat. No. 4,871,559, issued Oct. 3, 1989 to Dunn et al., titled METHODS FOR PRESERVATION OF FOODSTUFFS) teaches that the inactivation of enzymes by visible and infrared radiation utilizes a photo thermal mechanism. When applied at high-intensity and in combination, UV, IR, and visible light, which are components included in a complete spectrum, result in significant shelf life and stability enhancements of food products by the killing of microbes and by the inactivation of degradatory enzymes. Notably, the prior art for UV sterilization in biotechnology applications teaches away from Dunn's approach to multiple component light application; since the prior art teaches that filtered UV light is desirable while nonfiltered UV light is undesirable for sterilization of microorganisms, prior art teaches away from the use of non-filtered UV light for the sterilization of microorganisms. Disadvantageously, the activities of biotechnology products are frequently based on enzymatic activity or require the tertiary or quaternary structure of proteins for activity. Therefore, sterilization techniques like Dunn, that indiscriminately degrade proteins and enzymes in the process of sterilization, are not acceptable for use with biotechnology products. Thus, there remains a need for a sterilization technique that can effectively sterilize a biological product without denaturing the active biological products.

Therefore, there remains a need not solved by the prior art to more effectively sterilize a biological product of microorganisms without excessive denaturing of the active biological molecules.

BRIEF SUMMARY OF THE INVENTION

Accordingly, it has been discovered that a dichroic reflector utilized with a UV light source can overcome the limitations of the prior art. Therefore, the embodiments of the invention include the following.

In one embodiment, there is a system for sterilizing microorganisms on a heat sensitive liquid or solid substrate, the system comprising:
 a) a high intensity light source for producing a UV light;
 b) a dichroic reflector positioned proximate the light source, wherein the dichroic reflector is configured to focus the reflected light produced by the light source to a first end of light guide wherein the light guide delivers the light at a second end to provide a high intensity light output to the liquid or solid substrate; and wherein the dichroic reflector is configured to pass thermal energy produced by the light source through the dichroic reflector; and reflect the light produced by the light source to the light guide;
 c) a power supply, wherein the power supply is coupled to the light source;
 d) the light guide for receiving the high intensity light output focused from the dichroic reflector and deliver it from the light guide second end to the heat sensitive liquid or solid; and wherein the microorganisms within the range of the high intensity light output from the light guide are killed.

BRIEF SUMMARY OF SOME EXAMPLE EMBODIMENTS

This summary is provided to introduce a selection of concepts in a simplified form that are further described below in the detailed description. This summary is not intended to identify key features or essential characteristics of the claimed subject matter, nor is it intended to be used as an aid in determining the scope of the claimed subject matter.

One example embodiment includes a device for sterilizing microorganisms. The device includes a light source for producing a light and an optical device positioned proximate the light source. The optical device is configured to focus the light generated by the light source to provide a high intensity light output. The optical device also includes a dichroic reflector. The dichroic reflector is configured to pass thermal energy generated by the light source and reflect the light produced by the light source. The device also includes a power supply, where the power supply is coupled to the light source and the optical device. The device thereby killing microbial organisms presented within the range of the high intensity light output.

In one embodiment, the microbiological sterilization device includes a flexible fluid-core light guide. The flexible fluid-core light guide includes a first end and a second end. The flexible fluid-core light guide also includes a tubular body. The light guide is configured to be positioned and connected with the first end proximate to the optical device such that the high intensity light output is configured to be focused into the first end of the fluid-core light guide and channeled through the tubular body toward and out through the second end onto the substrate to be sterilized.

Another example embodiment includes a method for providing microbiological sterilization. The method includes providing a device for sterilizing microorganisms. The device includes a polychromatic light source for producing a polychromatic light and an optical device positioned proximate the polychromatic light source. The optical device is configured to focus the polychromatic light generated by the polychromatic light source to provide a high intensity light output of approximately 0.5 J/cm$^2$. The optical device also includes a dichroic reflector. The dichroic reflector is configured to pass thermal energy generated by the light source and reflect the light produced by the light source. The device also includes a power supply, where the power supply is coupled to the polychromatic light source and the optical device. The method also includes activating the polychromatic light source for a predetermined period of time to provide an exposure period greater than approximately 0.01 seconds. The method further includes positioning the device a predetermined distance from a substrate to be treated. The method additionally includes exposing the substrate to be treated to the high intensity light output. The method moreover includes deactivating the polychromatic light source, having sterilized any microbiological agents existing on the substrate.

These and other objects and features of the present invention will become more fully apparent from the following description and appended claims, or may be learned by the practice of the invention as set forth hereinafter.

BRIEF DESCRIPTION OF THE DRAWINGS

To further clarify various aspects of some example embodiments of the present invention, a more particular description of the invention will be rendered by reference to specific embodiments thereof, which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE INVENTION

Figure 1:
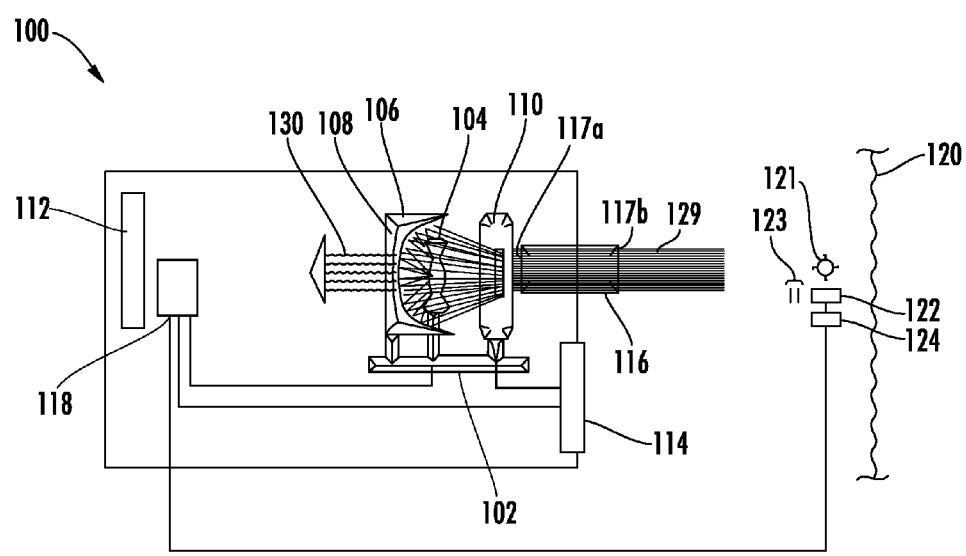
FIG. 1 illustrates a side view of the device for microbial sterilization.

References will now be made to the figures, wherein like structures will be provided with like reference designations. It is understood that the figures are diagrammatic and schematic representations of some embodiments of the invention, and are not limiting of the present invention, nor are they necessarily drawn to scale.

While this invention is susceptible to embodiment in many different forms, there is shown in the drawings, and will herein be described in detail, specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

DEFINITIONS

The terms "about", "essentially" and "approximately" mean±10 percent.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

The term "comprising" is not intended to limit inventions to only claiming the present invention with such comprising language. Any invention using the term comprising could be separated into one or more claims using "consisting" or "consisting of" claim language and is so intended.

References throughout this document to "one embodiment", "certain embodiments", and "an embodiment" or similar terms means that a particular feature, structure, or characteristic described in connection with the embodiment is included in at least one embodiment of the present invention. Thus, the appearances of such phrases in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitations thereto. The term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used in the specification and the claims, the phrase "configured to" denotes an actual state of configuration that fundamentally ties recited elements to the physical characteristics of the recited structure. That is, the phrase "configured to" denotes that the element is structurally capable of performing the cited element but need not necessarily be doing so at any given time. As a result, the phrase "configured to" reaches well beyond merely describing functional language or intended use since the phrase actively recites an actual state of configuration.

As used herein, the term "device for sterilizing microorganisms on a solid or liquid substrate" refers to a device that has a light source producing a wide spectrum of light capable of killing a microorganism, such as a bacteria or virus that is on a solid or liquid substrate. In particular, it produces a wide UV spectrum (i.e. more than just an isolated wavelength) even though it can produce other spectrums of light and, in one embodiment, the light produces a high UV output. Solid and liquid substrates refer to non-gas substrates, such as liquids, blood, skin, bone, organs, or inanimate liquids/solids.

As used herein, the term "light source" refers to a bulb of any kind which produces a sterilizing UV light. This can be UVA, UVB, UVC, or a combination. Regular bulbs, but also high intensity discharge (HID) bulbs, are also embodiments of the invention. So, for example, a high intensity mercury xenon (HgXe) bulb can be utilized. These types of bulbs are high UV output bulbs. In general, the light output of some bulbs of the invention are from about 0.1 J/cm$^2$ to about 50.0 J/cm$^2$. It also includes arc type lamps when they are focused properly.

As used herein, the term "optical device" refers to a device that collects light reflected off of the dichroic reflector and focuses the light into a high output stream. The focusing creates a high intensity light output. The device can be electric powered or have a manual way to focus the light.

As used herein, the term "high intensity light output" refers to light output of about at least 80 lumens per watt output in order to achieve this high intensity light output, one cannot use low or medium pressure lamps that produce UV light, as they do not produce enough light output. An arc discharge lamp produces does not produce the level of light output intensity needed. In order to achieve the high intensity output needed, one can add to the arc discharge lamp's light output an elliptical reflector which collimates the polychromatic light into still greater intensity (intensity being understood as energy per area) of about 100 lumens per watt (i.e. producing the high intensity light output needed).

As used herein, the term "dichroic reflector" refers to any of a dichroic focus, reflector, mirror, lens or the like that takes light from the light source and allows some or all of the thermal energy to pass through the reflector while taking the light, especially the UV light, to be reflected for focusing. In one embodiment, there may be more than one dichroic reflector but at least one must focus the light to the light pipe. The dichroic reflector can be any shape that works to either remove heat or focus the light but, in one embodiment, it is an elliptical shape for focusing. In one embodiment, an elliptical dichroic reflector is used with an arc lamp. This is different from a dichroic filter which only filters or reflects light but does not pass heat wavelengths through it. the dichroic filter can be a powered or unpowered device.

As used herein, the term "power supply" refers to an AC or DC source that powers the light supply and, where needed, the optical device or any other part of the device.

As used herein, the term "polychromatic" refers to light comprising multiple wavelengths of light.

As used herein, the term "predetermined exposure period" refers to the time period that light produced by the device is shown on a microorganism in order to kill it. In one embodiment, it is from about 0.01 seconds to about 5 seconds. In one embodiment, a shutter is utilized to open, close, and modulate the passage of light from the light source to the microorganism.

As used herein, the term "fluid-core light guide" refers to a light guide for taking light emitting from the focusing device and helping to deliver it to a product substrate or patient as needed. While the guide is not necessary to use the invention, it is an embodiment that helps focus or make it easier to deliver the focused light to a desired location/substrate, patient, or the like. The guide is generally a tube having a first and a second end of the tube, wherein the first end is used to collect light outputting from the device when positioned proximate to the device, such that the light channels through the tube and is delivered to the second end and out thereof, to deliver light where desired e.g. a substrate. The light guide could include a collimator. The light guide can be at least one of: flexible, UV transmissive, have or be a liquid, have an aqueous salt solution, have a metallic salt solution, wherein, in one embodiment, the metallic salt is Na, K, Mg or combinations thereof, a non-aqueous solution, or a gas.

The present invention relates generally to microbial sterilization (or DNA disruption, DNA inactivation), and more particularly to microbial sterilization using brief pulses of high-intensity polychromatic light directed optionally through a flexible, infrared-absorbing light guide. One of the objects of the present invention is to improve on the prior art by more effectively sterilizing a biological substrate, a product, or any substrate of microorganisms without excessive denaturing of any of the active biological molecules. (e.g. sterilizing microorganisms on a patient body surface). A further object of the present invention is the use of a shutter mechanism for the modulation of the exposure period to polychromatic, full spectrum light. A further object of the present invention is the use of a dichroic reflector for removal of thermal energy and the focusing (concentrating) of polychromatic, full spectrum light. A further object of the present invention is the use of an electronic circuit board for modulating lamp power, thermals and shutter timer of polychromatic, full spectrum light.

Thus, it is one aspect of the present invention to provide an apparatus that will sterilize biological, non-biological, or other products by way of high-intensity polychromatic or broad spectrum light irradiation, including UV-irradiation. It is another aspect of the present invention to provide an apparatus using light that has been filtered through a fluid to absorb the infrared region of the light spectrum, in order to minimize the photo thermal denaturing of the desirable elements of the irradiated object. We contend that those structures, such as muscle, fat, bone, hair, fluid, plant and fungus structures, are affected by such light. Additionally, non-biological materials, such as plastics, are also affected by germicidal light aimed at DNA disruption and our design provides less destructive effects. With the removal of the heat associated with such treatments, biological surfaces and other surfaces and substrates are spared.

An embodiment of the invention provides a device for microbial sterilization, generally referenced 100, as shown in FIG. 1. FIG. 1 shows that the device for microbial sterilization 100 can include: a power supply 102; a UV light source 104; at least one optical device 106 (which, in this embodiment, includes a dichroic reflector 108); a light shutter mechanism 110; a cooling fan 112; a timer 114; a light guide or light guide-conducting device 116 (that also functions as an infrared light filter) with a first end 117a and a second end 117b; and an exposure control system 118 to assure proper operation. Also featured are UV-sensitive diodes in a light-screened box 122, a detector circuit 124, as well as a neutral density filter and a UV-selective filter 123. FIG. 1 also shows the invisible infrared light (radiated heat) 130, a beam of incident light 129, a microorganism 121, and a substrate 120. The components of the embodiment are configured, positioned, and connected such that the power supply 102, in this embodiment consisting of an electronic circuit board, provides energy to the system. In particular, the power supply provides energy to the UV light source 104, which emits a light that is reflected off the at least one optical device 106, and otherwise focused or directed into the light guide 116. The dichroic reflector 108 provides a means for removing heat from the system. The cooling fan 112 provides another means for removing excess heat from the system. The shutter mechanism 110, timer 114, and control system 118 are interconnected to provide a controlled on/off light output which reaches the substrate 120 having microorganisms 121.

In one embodiment, the present invention includes a power supply 102 consisting of an electronic circuit board; a mercury xenon (HgXe) lamp as the UV light source 104; an elliptical dichroic reflector 108 in an optical device 106; a light shutter mechanism 110; a light guide 116 that also functions as an infrared light filter; and a control system 118. In one embodiment, the power supply 102 consists of a ballast that provides electricity at the appropriate voltage and amperage to power the ultraviolet (UV) light source 104. In another embodiment, the power supply 102 consists of a transformer to supply electricity at the proper voltage and amperage to power the UV light source 104. In another embodiment, the power supply 102 is an electronic circuit board (PCB) that provides electricity at the appropriate voltage and amperage to power the ultraviolet (UV) light source/lamp 104. The electronic circuit board connects other electronic equipment to, typically, a lamp igniter associated with a power supply. The lamp igniter delivers 8-12 amps to start the lamp. The power supply holds the lamp output with approximately 3-5 amps for a 100 W Hg or Hg/Xe lamp.

In one embodiment, the UV light source 104 is an HgXe vapor lamp, although other sources of UV light are also envisioned. The HgXe lamp is of a sufficient intensity to supply an energy density of between about 0.01 Joules per centimeter squared ($J/cm^2$) to about 50 $J/cm^2$ in a wavelength of between approximately 170 nanometers (nm) to approximately 2600 nm depending on the microorganism 121 to be sterilized. In another embodiment, the energy density impinging on the microorganism 121 to be sterilized is about 0.5 $J/cm^2$. Advantageously, the lamp is cooled by the continuous flow of air or a fluid, preferably water, directed over the lamp at a rate sufficient to prevent the lamp from overheating.

Additionally, the dichroic reflector 108 assists in dissipation from the lamp 104. Dichroic reflectors tend to be characterized by the color(s) of light that they are configured to reflect, rather than the color(s) they pass, as opposed to dichroic filters, thin-film filters, or interference filters, which are very accurate color filters characterized by the colors of light they selectively pass. The dichroic reflector 108 can be used behind the light source/lamp 104 to reflect visible (or other desired) light 129 forward while allowing the invisible infrared light (radiated heat) 130 to pass out of the rear of the device 100, resulting in a beam of light 129 that is literally cooler (of lower thermal temperature) i.e. there is an 80% reduction of thermals. Such an arrangement allows a given light 129 to dramatically increase its forward intensity while allowing the heat generated 130 by the backward-facing part of the device 100 to escape. In one embodiment, the dichroic reflector 108 is elliptical shaped. The dichroic surface of the reflector 108 is constructed of a sufficient surface coating to allow for the majority of incident light 129 to reflect, while allowing thermal light 130 to pass. The elliptical shape is designed such that a majority of the light emitted by the light source 104 that strikes the reflector 108 is reflected and focused towards the first end 117*a* of the light-conducting device 116.

Light exposure period modulation has traditionally been done through modulating the electrical current to a lamp. This type of exposure control system using electrical current is relatively economical and has therefore gained wide acceptance. However, continual flashing of the light source/lamp due to the current being turned on and off is detrimental to the light source/lamp, and results in a shorter lamp life. Therefore, the light source/lamp 104 is maintained in continuous excitation during use and light exposure modulation occurs through shutter mechanism 110. Shutter mechanism 110 can deliver exposure periods of between about 0.01 seconds to about 5 seconds, preferably between about 0.1 seconds and about 3 seconds, more preferably about 3 seconds. In addition, the shutter mechanism 110 can deliver these exposure periods in a repetitive manner in order to achieve a total exposure time sufficient to sterilize the microorganisms 121. The low exposure time can be critical to ensure that sterilization occurs without damaging the underlying substrate 120. Preferably, this exposure interval is typically in the range from about 0.01 to about 3 seconds, preferably 0.1 seconds.

The light-conducting device 116 is a fluid-core light guide consisting of a tube with a fluid core, having a first end 117*a* and a second end 117*b*. The tube in light guide 116 is a flexible, hollow tube, the walls of which are composed of a highly reflective material, of at least as high or higher reflectivity as the contained fluid itself, thereby increasing transmissivity within the light guide 116, or at least maintaining the transmissivity of the fluid itself. Additionally, the highly reflective material used in the tube walls has a diffraction coefficient sufficient such that the majority of light in the 200 nm to 1200 nm range transmitted through the fluid core of the tube is reflected back into the fluid core, should it contact the walls of the tube.

In light-conducting device 116 the fluid core is composed of a gas, an aqueous metallic salt solution (or some other aqueous solution), or a non-aqueous solution. The fluid in fluid-core light guide 116 is formulated such that it absorbs infrared light that may be emitted by the HgXe lamp/light source 104 and transmitted into the fluid-core light guide 116. In one embodiment, the fluid is a non-aqueous solution composed of organic fluids. Organic fluids are desirable for this use since they have high infrared (IR) absorptivity, and infrared light can damage the proteins, enzymes and cell components of a microorganism 121, precluding the viability of a sterilized organism for use as a vaccine. In another embodiment, the fluid is an aqueous metallic salt solution, such as an aqueous sodium chloride (NaCl) solution—although the salt may also be selected from the group consisting of KCl, MgCl, $MgSO_4$, other organics, and the like. The concentration of NaCl is between about 5% to about 50%. Preferably, the concentration can range between about 5% to about 10%.

The ends 117*a* and 117*b* of the light guide 116 may be fabricated from translucent quartz, fused silica, or synthetic or natural diamond, all of which do not absorb UV light. The light guide 116 directs the exiting light out of second end 117*b* towards the microorganism 121 which is on substrate 120. Additionally, a dichroic reflector 108, of an appropriate shape is used to focus reflected light on the microorganism 121 which is on substrate 120 while passing thermal energy 130 away from the substrate 120 to prevent damage to the substrate 120 while sterilizing the microorganism 121.

The proper functioning of the sterilizing device 100 is assured by a control system 118. The control system 118 is composed of a UV-sensitive diode placed in a light-screened box 122 juxtaposed to the microorganism 121 on the substrate 120. The UV sensitive diode 122 is coupled to a detector circuit 124 that provides an output indicative of the amount of light impinging upon the UV-sensitive diode 122 during the exposure period. A neutral density filter and a UV-selective filter 123 are interposed between the light guide 116 and the UV-sensitive diode 122 in order to attenuate the light and to impede passage of wavelengths outside the UV range, respectively. In the event that the detector circuit 124 detects that the light impinging on the UV-sensitive diode 122 is below a sufficient level, the power delivered to the light source/lamp 104 (which could be a flash lamp, gas lamp, etc.) may be increased, the exposure period may be lengthened, or the sterilization operation may be suspended until the device 100 can be serviced.

In another embodiment, an alternate means of controlling the amount of UV light landing on the microorganism 121 on the substrate 120 is to use a control system 118 as above, but instead of measuring the UV light impinging on a UV-sensitive diode 122, the detector circuit 124 is paired with a means to measure the fluorescence emitted by the microorganism 121. It is understood that fluorescence is a key factor in the effectiveness of this device for microbial sterilization using polychromatic light for inactivation of microorganisms. Fluorescence is an indication of an activated state, and is the result of absorbing high-energy radiation that is then emitted at a low energy wavelength. An activated state is believed to be associated with a greater chemical reactivity, and thus is believed to favor the formation of cyclobutane dimers in the genome of the cell or microorganism.

The device for microbial sterilization 100 according to the present invention has virtually unlimited application. By way of example, not of limitation, the device can be used for the inactivation and or sterilization of all known pathogens, including viruses (such as herpes simplex virus and HIV), bacteria (such as *E. coli* and *Staphylococcus* spp.), and fungi (such as Candidiasis) by creating vaccines from the sterilized microorganism(s).

Also advantageously, the device for microbial sterilization 100, according to the present invention, can be used to sterilize remote or large fixed substrates. By constructing the device 100 of such materials and technology as to make the device portable by a person, the device 100 can be used to rapidly sterilize remote or large substrate areas. In such an embodiment, a person, in this case a sterilization administrator, can sterilize a large substrate area with ease by simply maintaining the direction of the light guide 116 towards the substrate and the moving the light 129 over the substrate area while the sterilization administrator potentially moves or walks around.

Figure 2:
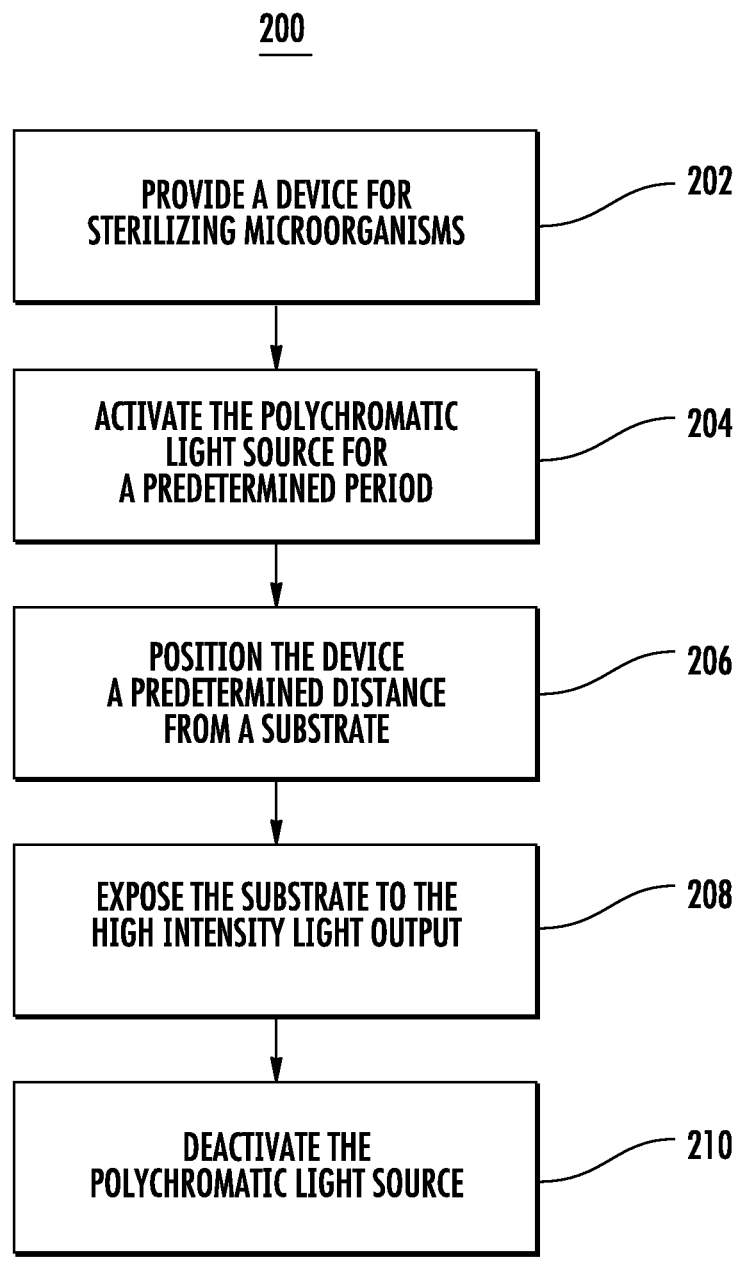
FIG. 2 is a flowchart illustrating a method for providing microbiological sterilization.

FIG. 2 is a flow chart illustrating a method 200 for providing microbiological sterilization. The method allows for sterilization of any desired substrate without damaging structures such as muscle, fat, bone, hair, fluid, plant and fungus structures. In particular, harmful portions of high intensity light have been eliminated such that the resulting output only damages microorganisms without damaging the underlying structure.

FIG. 2 shows that the method can include providing 202 a device for sterilizing microorganisms. For example, the device for sterilizing microorganisms can include the device 100, reference above with respect to FIG. 1. Therefore, the method 200 will be described, exemplarily, with reference to the device 100 of FIG. 1. Nevertheless, one of skill in the art can appreciate that the method 200 can be used with a device other than the device 100 of FIG. 1.

FIG. 2 also shows that the method 200 can include activating 204 the polychromatic light source for a predetermined period to provide an exposure period greater than about 0.01 seconds. For example, the exposure period can be from 0.01 seconds and about 5 seconds, preferably between about 0.1 seconds and about 3 seconds, more preferably about 3 seconds. In addition, a shutter mechanism can deliver these exposure periods in a repetitive manner in order to achieve a total exposure time sufficient to sterilize the microorganisms.

FIG. 2 further shows that the method 200 can include positioning 206 the device a predetermined distance from a substrate to be treated. For example, the device can be positioned 206 approximately 2.25 inches away from the substrate. The distance can be adjusted based on the substrate being treated, the intensity of the output, the microorganisms being sterilized and other facts.

FIG. 2 additionally shows that the method 200 can include exposing 208 the substrate to be treated to the high intensity light output. That is, the high intensity light output is directed onto the substrate, sterilizing the microorganisms thereon. The exposure can include constant exposure or a "sweep" that moves the high intensity light output along the substrate.

FIG. 2 moreover shows that the method 200 can include deactivating 210 the polychromatic light source, having sterilized any microbiological agents existing on the substrate. That is, once the microorganisms have been sterilized the light source is turned off and the substrate is now sterilized for the desired use One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Having described the present invention, various aspects of the invention having more specific preferred embodiments and examples will now be described in greater detail by way of the following specific examples. These examples demonstrate quantitatively the effectiveness of the invention for preserving biotechnology products by reducing or eliminating microorganisms. In these examples, microorganisms were deliberately introduced into the product to be treated. The deliberate introduction of high counts of microorganisms to a product results in a high degree of self-shielding of the microorganisms, requiring an increased exposure time to the sterilizing light over routine counts of microorganisms. Therefore, these examples represent a dramatic demonstration of the effectiveness of the high-intensity light treatment.

Example 1

This example is based upon an experiment conducted with a fluid-filled light guide, available commercially from Edmund Scientific®, clamped to a position with the light emitting end of the light guide substantially perpendicular to the substrate to be exposed and sterilized, approximately 2.25 inches away from the substrate. The fluid-filled light guide was connected to an aperture housing and shutter mechanism positioned in front of and coupled with a light source, in this experiment the light source is a high power, 1 kilowatt mercury-xenon (HgXe) lamp, available commercially from the LESCO UV division of American Ultraviolet©. Herpes virus (HSV) cultures were prepared from herpes-virus infected cells by dilution of culture supernatant into cell culture media at a dilution sufficient to provide $10^6$ plaque-forming units (PFUs)/mL. An aliquot of approximately 10 mL was exposed to UV light, at a distance 2.25" from the device, according to one embodiment, for a period of 3 seconds. After the exposure period, triplicate samples of 2 mL were taken from the treated sample and applied to freshly prepared HSV cells and incubated at 37° C. for 72 hours. Upon examination at 3 days, no plaques were observed in the treated samples, whereas the positive control samples were observed to have a titer of $10^6$ PFUS/mL; thus, at the start of the experiment, $10^6$ PFUs/mL were treated for 3 seconds in one embodiment, according to the present invention, resulting in zero (0) PFUs/mL after exposure with the high intensity light source.

Additionally, a semi-quantitative inactivation of bacteria, and other viruses, including but not limited to *E. coli*, *Staphylococcus* spp., and Klebsiella culture, were sterilized with UV-light. These are set forth by way of example and not of limitation. Other bacteria, like those commonly found in households, ventilation, fecal matter, human mouths, and the like, will be similarly inactivated and sterilized when exposed to the device according to the present invention, in a similar manner and similar conditions to those set forth in Example 1.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fall within the scope of the invention as claimed by the applicant.

What is claimed is:

1. A system for generating a low thermal energy high intensity UV light for sterilizing microorganisms on a heat sensitive liquid or solid substrate, the system comprising:
   a) a high intensity light source for producing a UV light;
   b) at least one dichroic reflector positioned proximate the light source, wherein the dichroic reflector is configured to focus the reflected light produced by the light source to provide a low thermal energy high intensity light output to be delivered to the liquid or solid substrate; and wherein the dichroic reflector is configured to pass thermal energy produced by the light source through the dichroic reflector; and reflect the low thermal energy high intensity UV light; and
   c) a power supply, wherein the power supply is coupled to the light source; and
   wherein the microorganisms within the range of the delivered high intensity light output are killed.

2. The system according to claim 1, wherein the light source is polychromatic.

3. The system according to claim 1, wherein the dichroic reflector is elliptical.

4. The system according to claim 3, wherein the light source includes a high intensity HgXe lamp.

5. The system according to claim 1 wherein the light source is a high UV output light source.

6. The system according to claim 1, wherein the light source is activated for a predetermined exposure period just sufficient to kill the microorganism.

7. The system according to claim 6, wherein the exposure period is greater than approximately 0.01 seconds.

8. The system according to claim 7, wherein the exposure period is between approximately 0.01 seconds and approximately 5 seconds.

9. The system according to claim 6, further comprising a shutter mechanism, wherein the shutter mechanism is positioned and connected proximate to the optical device for controlling the exposure period by modulating the light source.

10. The system according to claim 1, wherein the power supply includes an electronic ballast that is configured to regulate heat removal.

11. The system according to claim 1, wherein the light source is an arc lamp.

12. The system according to claim 1 which comprises one or more additional dichroic filters.

13. A method for providing a low thermal energy, high intensity UV light for microbial sterilization on a heat sensitive substrate comprising the steps of:
   a. providing a device which produces a low thermal energy, high intensity UV light, wherein the device includes:
      i. a high intensity light source for producing a UV light;
      ii. at least one dichroic reflector positioned proximate the light source, wherein the dichroic reflector is configured to focus the reflected light produced by the light source and wherein the at least one dichroic reflector is configured to pass thermal energy produced by the light source through the dichroic reflector; and
      iii. a power supply configured to couple the light source;
   b. activating the light source; and
   c. taking the focused light and delivering it to the substrate to expose the substrate to the low thermal energy, high intensity UV light.

14. A method for delivering a high energy UV light to a substrate comprising:
   a. selecting a high energy light that emits a high energy UV light;
   b. removing the thermal energy produced by the high energy UV light; and
   c. delivering the high energy light without thermal energy to the substrate.

* * * * *